US010813657B2

(12) United States Patent
Govari et al.

(10) Patent No.: US 10,813,657 B2
(45) Date of Patent: Oct. 27, 2020

(54) DEBRIDER WARNING SYSTEM

(71) Applicant: Biosense Webster (Israel) Ltd., Yokneam (IL)

(72) Inventors: Assaf Govari, Haifa (IL); Yehuda Algawi, Binyamina (IL); Vadim Gliner, Haifa (IL); Yaron Ephrath, Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 169 days.

(21) Appl. No.: 15/730,578

(22) Filed: Oct. 11, 2017

(65) Prior Publication Data

US 2019/0105072 A1    Apr. 11, 2019

(51) Int. Cl.
*A61B 17/32* (2006.01)
*A61B 34/20* (2016.01)
(Continued)

(52) U.S. Cl.
CPC .......... *A61B 17/320016* (2013.01); *A61B 17/32002* (2013.01); *A61B 34/20* (2016.02); *A61B 17/24* (2013.01); *A61B 34/25* (2016.02); *A61B 2017/00115* (2013.01); *A61B 2017/00119* (2013.01); *A61B 2017/00199* (2013.01); *A61B 2017/320024* (2013.01);
(Continued)

(58) Field of Classification Search
CPC ............ A61B 17/320016; A61B 34/20; A61B 17/32002; A61B 2034/2065; A61B 2034/2051; A61B 2090/3762; A61B 2090/364; A61B 17/24; A61B 2017/320024; A61B 2017/00199; A61B 2017/00119; A61B 2017/00115; A61B 34/25

USPC ........................................................ 382/128
See application file for complete search history.

(56) References Cited

U.S. PATENT DOCUMENTS 5,391,199 A    2/1995    Ben-Haim
5,443,489 A    8/1995    Ben-Haim
(Continued)

FOREIGN PATENT DOCUMENTS

WO    WO-2006097911 A1 *  9/2006 ............... G06T 7/11

OTHER PUBLICATIONS

Extended European Search Report dated Feb. 20, 2019 for Application No. 18199917.8, 12 pages.

*Primary Examiner* — Amandeep Saini
(74) *Attorney, Agent, or Firm* — Frost Brown Todd LLC

(57) ABSTRACT

Apparatus, including a tube having a proximal end, and a distal end for insertion into a body cavity including anatomical structures, and a blade mounted at the distal end. The apparatus also includes a handle at the proximal end and including a device which generates sensible outputs upon receiving activation signals, and a position sensor fixed in a predefined disposition relative to the tube. The apparatus additionally includes a processor configured to acquire an image of the cavity, to determine, in the image, locations for each of the structures, to receive, from the sensor, a position signal indicative of a blade location of the blade within the cavity, to determine, based on the blade location and the respective structure locations, a proximity of the blade to a given structure, and to convey, to the warning device, a given activation signal in response to the proximity to the given structure.

25 Claims, 4 Drawing Sheets

(51) Int. Cl.
  *A61B 17/00*   (2006.01)
  *A61B 17/24*   (2006.01)
  *A61B 90/00*   (2016.01)
  *A61B 34/00*   (2016.01)

(52) U.S. Cl.
  CPC .............. *A61B 2034/2051* (2016.02); *A61B 2034/2065* (2016.02); *A61B 2090/364* (2016.02); *A61B 2090/3762* (2016.02)

(56) References Cited

U.S. PATENT DOCUMENTS

| | | |
|---|---|---|
| 5,558,091 A | 9/1996 | Acker et al. |
| 6,172,499 B1 | 1/2001 | Ashe |
| 6,177,792 B1 | 1/2001 | Govari et al. |
| 6,690,963 B2 | 2/2004 | Ben-Haim et al. |
| 6,788,967 B2 | 9/2004 | Ben-Haim et al. |
| 7,559,925 B2 | 7/2009 | Goldfarb et al. |
| 7,720,521 B2 | 5/2010 | Chang et al. |
| 2005/0054900 A1 | 5/2005 | Mawn et al. |
| 2006/0004286 A1* | 1/2006 | Chang ................ A61B 5/06 600/435 |
| 2008/0118725 A1 | 5/2008 | Lloyd |
| 2008/0183188 A1 | 7/2008 | Carls et al. |
| 2013/0163836 A1* | 6/2013 | Pau ................ G06T 7/00 382/128 |
| 2014/0272772 A1* | 9/2014 | Andreiko ........... A61C 7/002 433/29 |
| 2015/0342500 A1* | 12/2015 | Fujita ............... G02B 23/24 600/117 |
| 2016/0074123 A1 | 3/2016 | Bly et al. |
| 2016/0220314 A1* | 8/2016 | Huelman .......... A61B 34/20 |
| 2016/0242855 A1* | 8/2016 | Fichtinger ........ A61B 34/20 |
| 2017/0156799 A1* | 6/2017 | Bozung ........... A61B 17/32002 |
| 2018/0247437 A1* | 8/2018 | Hoornaert ......... A61B 6/5264 |

* cited by examiner

US 10,813,657 B2

DEBRIDER WARNING SYSTEM

FIELD OF THE INVENTION

The present invention relates generally to medical probes, and specifically to an invasive medical probe comprising a cutting end.

BACKGROUND OF THE INVENTION

Some medical probes (e.g., debriders) include cutting blades (also known as cutting ends) that can be used to remove tissue during an invasive medical procedure. These medical probes typically include position sensors that can be used to keep track of the current location and orientation of the cutting blade.

U.S. Pat. No. 7,720,521 to Chang et al., describes a device for performing procedures within an ear, nose, throat and a paranasal sinus. The device includes a sensor that can be used to determine a location of a treatment device (e.g., a needle, a debrider or a cutter) affixed to the device.

U.S. Patent Application 2008/0118725, now abandoned, to Lloyd, describes a system for visual verification of computed tomography (CT) registration and feedback. The system is configured to track different types of surgical devices inside a patient during a medical procedure.

U.S. Pat. No. 7,559,925 to Goldfarb et al., describes devices for facilitating visualization in a surgical environment. The devices include a fluoroscope, a first introducing device (e.g., a sinus guide, a guide catheter or a guide tube) that can be introduced under direct visualization (i.e., by the fluoroscope), a second introducing device (e.g., a guidewire or an elongated probe) and a working device (e.g., a balloon catheter, a dilatation catheter, a debrider, or a cutter).

U.S. Patent Application 2005/0054900 to Mawn et al., issued as U.S. Pat. No. 8,403,828 on Mar. 26, 2013, describes an ophthalmic orbital surgery apparatus and image-guided navigation system. The apparatus and system includes a flexible endoscope, a rigid endoscope having a magnetic tracking tip, and a magnetic tracking system configured to detect the magnetic tracking tip in three dimensional space, and to communicate the magnetic tracking tip location data to the apparatus for collecting and processing physical space data.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention, a medical apparatus, including an insertion tube having a proximal end, and a distal end for insertion into a body cavity including one or more anatomical structures. The medical apparatus also includes a cutting blade mounted at the distal end of the insertion tube, a handle affixed to the proximal end and including a warning device which generates different sensible outputs in response to receiving different activation signals, and a position sensor fixed in a predefined disposition relative to the insertion tube. The medical apparatus additionally includes a processor configured to acquire, from an imaging system, a three-dimensional (3D) image of the body cavity, to determine, in the 3D image, respective 3D structure locations for each of the one or more anatomical structures, to receive, from the position sensor, a position signal indicative of a 3D blade location of the cutting blade within the body cavity, to determine, based on the 3D blade location and the respective 3D structure locations, a proximity of the cutting blade to a given anatomical structure, and to convey, to the warning device, a given activation signal in response to the determined proximity to the given anatomical structure.

In some embodiments, the warning device is detachable from the handle. In additional embodiments, the warning device includes an illumination device or an audio generating device. In embodiments where the warning device includes an illumination device, the sensible output generated by the illumination device in response to the determined proximity to the given anatomical structure includes light having different colors, different intensities, or different durations. In embodiments where the warning device includes an audio generating device, the sensible output generated by the audio generating device in response to the determined proximity to the given anatomical structure includes sounds having different tones, different frequencies, different volumes, different durations, different rates of recurrence or different synthesized words.

The medical apparatus may include a display, and the processor may be configured to present, on the display, the sensible output in response to the determined proximity to the given anatomical structure. In further embodiments, the position sensor includes a triaxial coil. In supplemental embodiments, the imaging system includes a computed tomography scanner.

In some embodiments, the imaging system includes an image coordinate system, wherein the position sensor includes a sensor coordinate system, and wherein prior to receiving the position signal indicative of a 3D blade location of the cutting blade within the body cavity, the processor is configured to register the sensor coordinate system to the image coordinate system. In additional embodiments, the medical apparatus includes a motor mounted within the handle and configured to rotate the cutting blade at a plurality of rotation speeds, and wherein the processor is configured to reduce the rotation speed of the cutting blade as the cutting blade approaches a given anatomical structure.

In further embodiments, the anatomical structures in the 3D image include different tissue radiodensities, and wherein the processor is configured to determine a given 3D structure location by detecting the different radiodensities in the 3D image, segmenting, based on the detected different radiodensities, the 3D image into multiple segments, and determining respective 3D locations of the segments. In one embodiment, the processor is configured to formulate an identification of a given segment of the multiple segments, and wherein the activation signal includes the identification.

There is also provided, in accordance with an embodiment of the present invention, a method, including acquiring, from an imaging system, a three-dimensional (3D) image of a body cavity including one or more anatomical structures, determining, in the 3D image, respective 3D structure locations for each of the one or more anatomical structures, receiving, from a medical probe having an insertion tube and a position sensor fixed in a predefined disposition relative to the insertion tube, a position signal indicative of a 3D location of a cutting blade mounted at a distal end of the insertion tube and inserted into the body cavity, determining, by a processor based on the 3D blade location and the respective 3D structure locations, a proximity of the cutting blade to a given anatomical structure, conveying, to a warning device mounted on a handle affixed to a proximal end of the insertion tube and configured to generate different sensible outputs in response to receiving different activation signals, a given activation signal in response to the determined proximity to the given anatomical structure, receiving, by the warning device, the given activation signal, and generating, by the warning device, a given sensible output in response to the received activation signal.

There is additionally provided, in accordance with an embodiment of the present invention, a computer software product, operated in conjunction with a medical probe having an insertion tube and a position sensor fixed in a predefined disposition relative to the insertion tube, the product including a non-transitory computer-readable medium, in which program instructions are stored, which instructions, when read by a computer, cause the computer to acquire, from an imaging system, a three-dimensional (3D) image of a body cavity including one or more anatomical structures, to determine, in the 3D image, respective 3D structure locations for each of the one or more anatomical structures, to receive, from the position sensor, a position signal indicative of a 3D location of a cutting blade mounted at a distal end of the insertion tube and inserted into the body cavity, to determine, based on the 3D blade location and the respective 3D structure locations, a proximity of the cutting blade to a given anatomical structure, and to convey, to a warning device mounted on a handle affixed to a proximal end of the insertion tube and configured to generate a plurality of sensible outputs in response to receiving a corresponding plurality of activation signals, a given activation signal in response to the determined proximity to the given anatomical structure.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Invasive medical probes such as debriders may comprise cutting ends (e.g., a blade) that, during a medical procedure, may closely approach sensitive regions in a patient. Examples of sensitive regions include an eye, an optic nerve, the carotid artery, and the brain. Therefore, it is important to notify an operating physician when a cutting end of a medical probe approaches a given sensitive region. One method for tracking the cutting end is to use fluoroscopy, but because of its ionizing characteristic, the use of fluoroscopy should be minimized.

In embodiments of the present invention, an apparatus includes a medical probe (e.g., a debrider) that can be used to perform invasive medical procedures on a patient. The medical probe comprises an insertion tube comprising a proximal end, and a distal end for insertion into a body cavity having one or more anatomical structures. The medical probe also comprises a cutting blade mounted at the distal end of the insertion tube, and a handle affixed to the proximal end. The medical probe additionally comprises a warning device which generates different sensible outputs in response to receiving different activation signals, and a position sensor fixed in a predefined disposition relative to the insertion tube.

The apparatus also includes a processor configured to acquire, from an imaging system, a three-dimensional (3D) image of the body cavity, and to determine, in the 3D image, respective 3D structure locations for each of the one or more anatomical structures. The processor is further configured to receive, from the position sensor, a position signal indicative of a 3D blade location of the cutting blade within the body cavity, and to determine, based on the 3D blade location and the respective 3D structure locations, a proximity of the cutting blade to a given anatomical structure.

Upon determining that the cutting blade is in proximity to a given anatomical structure, the processor is configured to convey, to the warning device, a given activation signal in response to the determined proximity to the given anatomical structure, and the warning device is configured to generate a given sensible output upon receiving the given activation signal. The given sensible output may comprise a visual and/or an audial notification.

In embodiments described herein, the warning device can generate different sensible outputs for different distances between the cutting blade and the different anatomical structures. Therefore, medical systems implementing embodiments of the present invention can help prevent accidental damage to sensitive anatomical structures (e.g., arteries and nerves) during invasive medical procedures.

System Description

Figure 1A:
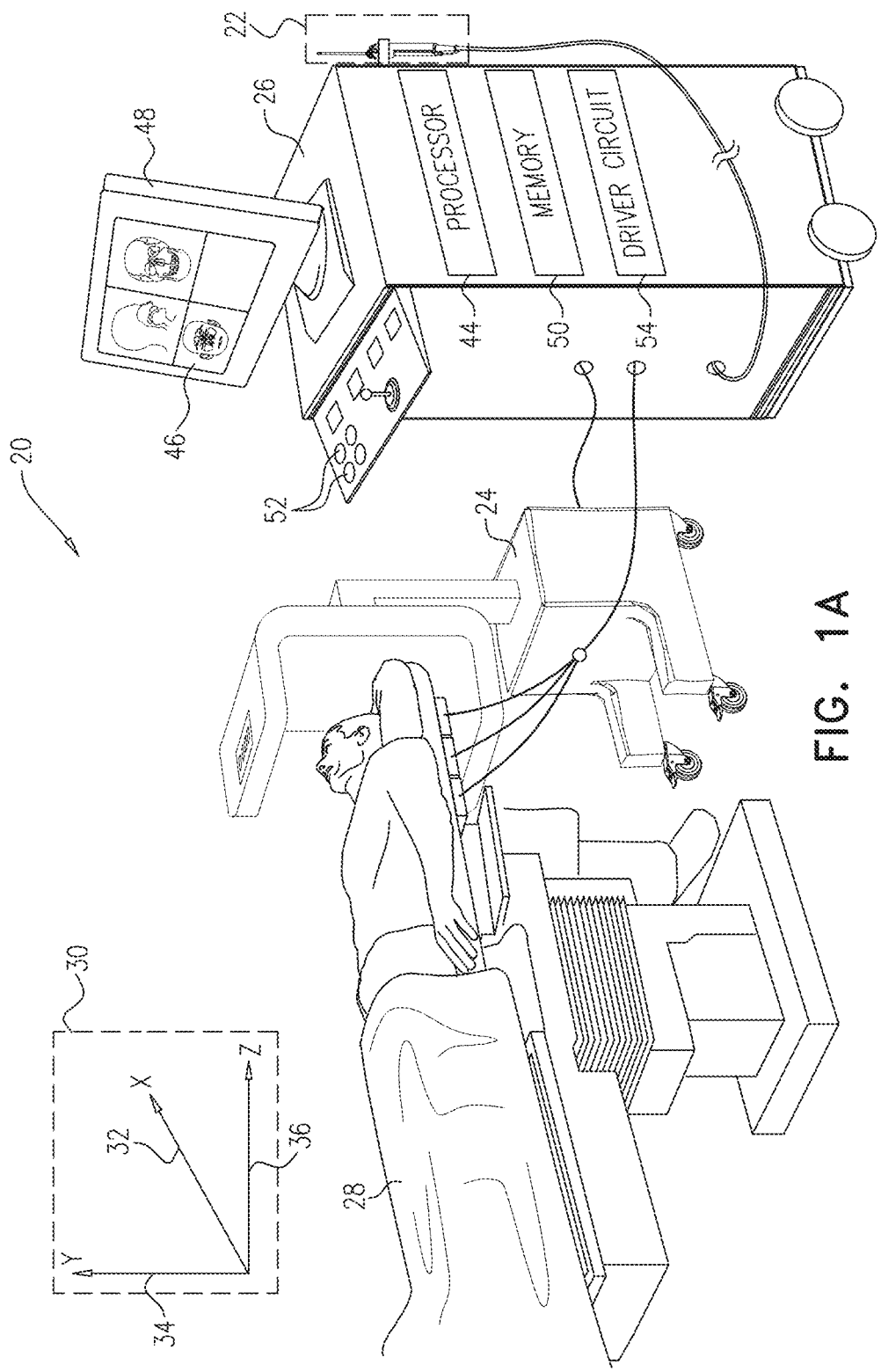
FIGS. 1A and 1B, referred to collectively as FIG. 1, are schematic pictorial illustrations of a medical system comprising a medical probe having a location-based warning module, in accordance with an embodiment of the present invention.
Figure 1B:
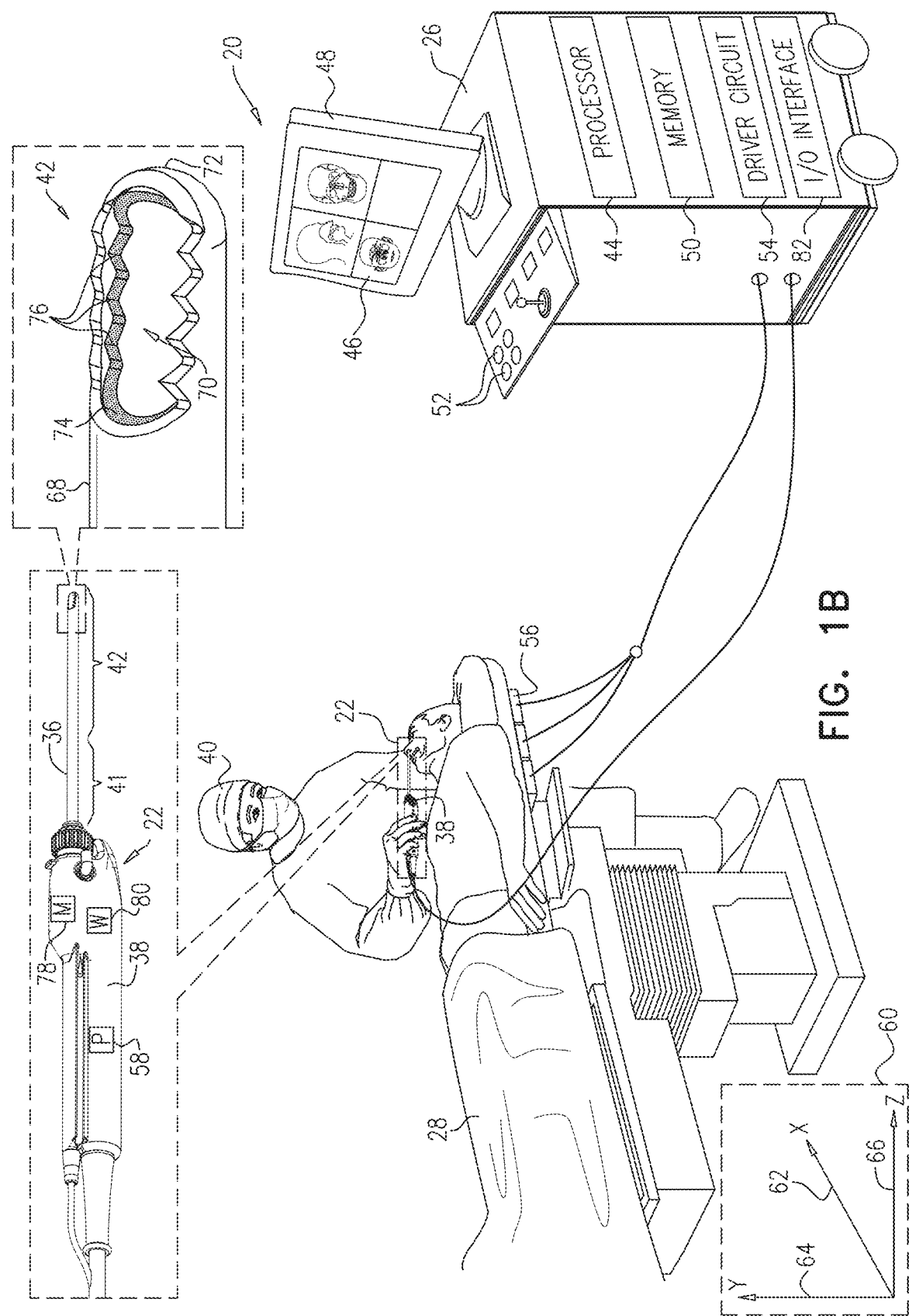

FIGS. 1A and 1B, referred to collectively as FIG. 1, are schematic pictorial illustrations of a medical system 20 comprising a medical probe 22 configured to generate location-based warnings, in accordance with an embodiment of the present invention. In the example shown in FIG. 1A, medical system 20 comprises a medical imaging system comprising a computed tomography (CT) scanner 24, a control console 26, and medical probe 22. In embodiments described herein, it is assumed that medical probe 22 is used for diagnostic or therapeutic treatment, such as minimally invasive catheter-based sinus surgery on a patient 28. Alternatively, medical probe 22 may be used, mutatis mutandis, for other therapeutic and/or diagnostic purposes.

Prior to performing an invasive medical procedure on patient 28, computed tomography scanner 24 generates electrical signals comprising image data for a lumen (e.g., a nasal cavity or a paranasal sinus) of the patient, and conveys the generated image data to control console 26. Computed tomography scanner 24 generates the image data in an image coordinate system 30 comprising an X-axis 32, a Y-axis 34 and a Z-axis 36.

As shown in FIG. 1B, medical probe 22 comprises a handle 38 that an operator 40 can grasp and manipulate in order to insert a distal end 42 of the medical probe into a lumen, such as a nasal cavity or a paranasal sinus, of patient 28. In the configuration shown in FIG. 1, control console 26 comprises a processor 44 that converts the received image data into an image 46, and presents the image as information regarding the medical procedure on a display 48.

Display 48 is assumed, by way of example, to comprise a flat panel display such as a liquid crystal display, a light emitting diode display, an organic light-emitting diode display or a plasma display. However, other display devices can also be employed to implement embodiments of the present invention. In some embodiments, display 48 may comprise a touchscreen that can be configured to accept inputs from operator 40, in addition to presenting image 46.

Based on the signals received from medical probe 22 and other components of medical system 20, control console 26 drives display 48 to update image 46 in order to present a current position of distal end 42 in the patient's body, as well as status information and guidance regarding the medical procedure that is in progress. Processor 44 stores data representing image 46 in a memory 50. In some embodiments, operator 40 can manipulate image 46 using one or more input devices 52. In embodiments where display 48 comprises a touchscreen display, operator 40 can manipulate image 46 via the touchscreen display.

Processor 44 typically comprises a general-purpose computer, with suitable front end and interface circuits for receiving signals from medical probe 22 and controlling the other components of control console 26. Processor 44 may be programmed in software to carry out the functions that are described herein. The software may be downloaded to control console 26 in electronic form, over a network, for example, or it may be provided on non-transitory tangible media, such as optical, magnetic or electronic memory media. Alternatively, some or all of the functions of processor 44 may be carried out by dedicated or programmable digital hardware components.

In embodiments described herein, medical system 20 uses magnetic position sensing to determine position coordinates (i.e., a location and an orientation) of distal end 42 of medical probe 22 inside patient 28. To implement magnetic based position sensing, control console 26 comprises a driver circuit 54 which drives field generators 56 to generate magnetic fields within the body of patient 26. Typically, field generators 56 comprise three orthogonally oriented coils, which are placed below the patient at known positions external to patient 28. These coils generate magnetic fields in a predefined working volume that contains a lumen such as a paranasal sinus. A magnetic field sensor 58 (typically a triaxial coil, also referred to herein as position sensor 58) fixed within handle 38 of medical probe 22 generates electrical signals in response to the magnetic fields from the generator coils, thereby enabling processor 44 to determine the position of distal end 42 within a lumen in patient 28, since there is a known displacement between sensor 58 and distal end 42.

The position of sensor 58, and thus of distal end 42, is determined with respect to a frame of reference 60, also referred to herein as sensor coordinate system 60, defined by field generators 56. In order to find the correspondence between the signals generated in sensor 58 and the position of the sensor, the field from generators 56 is calibrated, prior to positioning patient 28 in the field. The calibration typically comprises processor 44 acquiring calibration signals from a calibration sensor such as sensor 28, while the calibration sensor is positioned at known, measured, locations relative to generators 56. Processor 44 is then able to form a correspondence between the known locations and the calibration signals, and to use the correspondence to determine the location of sensor 58 in system 60 from the signals the sensor generates.

Additional magnetic position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference. The signals generated by magnetic field sensor 58 indicate the current location of distal end 42 in a sensor coordinate system 60 comprising an X-axis 62, a Y-axis 64 and a Z-axis 66. In the example shown in FIG. 1, X-axis 62 generally corresponds to X-axis 32, Y-axis 64 generally corresponds to Y-axis 34 and Z-axis 66 generally corresponds to Z-axis 36.

In the example shown in FIG. 1B, medical probe comprises an outer tube 68 (also referred to herein as an insertion tube) having a proximal end 41 affixed to handle 38, and a distal end 42 comprising a radial cutting window opening 70 in proximity to a distal tip 72 of the outer tube. Medical probe 22 also comprises an inner tube 74 that is positioned within outer tube 68 and comprises a cutting blade 76 (also known as a cutting end, since it is positioned at distal end 42). In operation, as cutting blade 76 traverses radial cutting window opening 70, the cutting blade can remove any body tissue protruding into the cutting window. Handle 38 also comprises a motor 78 that rotates inner tube 74 within outer tube 68, thereby enabling cutting blade 76 to traverse radial cutting window opening 70.

In the configuration shown in FIG. 1B, position sensor 58 is affixed to handle 38 in a predefined disposition relative to insertion tube 68 and cutting blade 76. In an alternative embodiment, position sensor 58 can be affixed to insertion tube 68 in a predefined disposition relative to cutting blade 76.

In addition to position sensor 58 and motor 78, handle 38 also comprises a warning device 80, and an input/output (I/O) communications interface 82 that enables the control console to transfer signals from, and/or transfer signals to driver circuit 54, position sensor 58, motor 78, and warning device 80. Driver circuit 54, position sensor 58, motor 78 and warning device 80 are all coupled to I/O interface 82 in control console 26 via wired connections (not shown) and/or wireless connections, thereby enabling the control console to (a) receive position signals from position sensor 58, (b) control the speed of motor 78, and (c) convey an activation signal to warning device 80.

Warning device 80 generates sensible outputs and comprises one or more illumination devices (e.g., light emitting diodes) that can convey a visual sensible output and/or an audio generating device (e.g., a speaker) that can generate an audible sensible output. In embodiments of the present invention, warning device 80 can convey different types of sensible outputs in response to different activation signals. In embodiments where warning device 80 comprises one or more illumination devices, the different types of sensible outputs may include different colors (e.g., green, yellow and blue), different intensities, different durations and different rates of recurrence (i.e., blinking). In embodiments where warning device 80 comprises a speaker, the different types of sensible outputs may include sounds having different tones/frequencies, different volumes, different durations, different rates of recurrence (i.e., beeping) and synthesized words (e.g., "Warning"). In some embodiments, warning device 80 may be removably attached (i.e., detachable) from handle 38.

Sensitive Region Warning Generation

Figure 2:
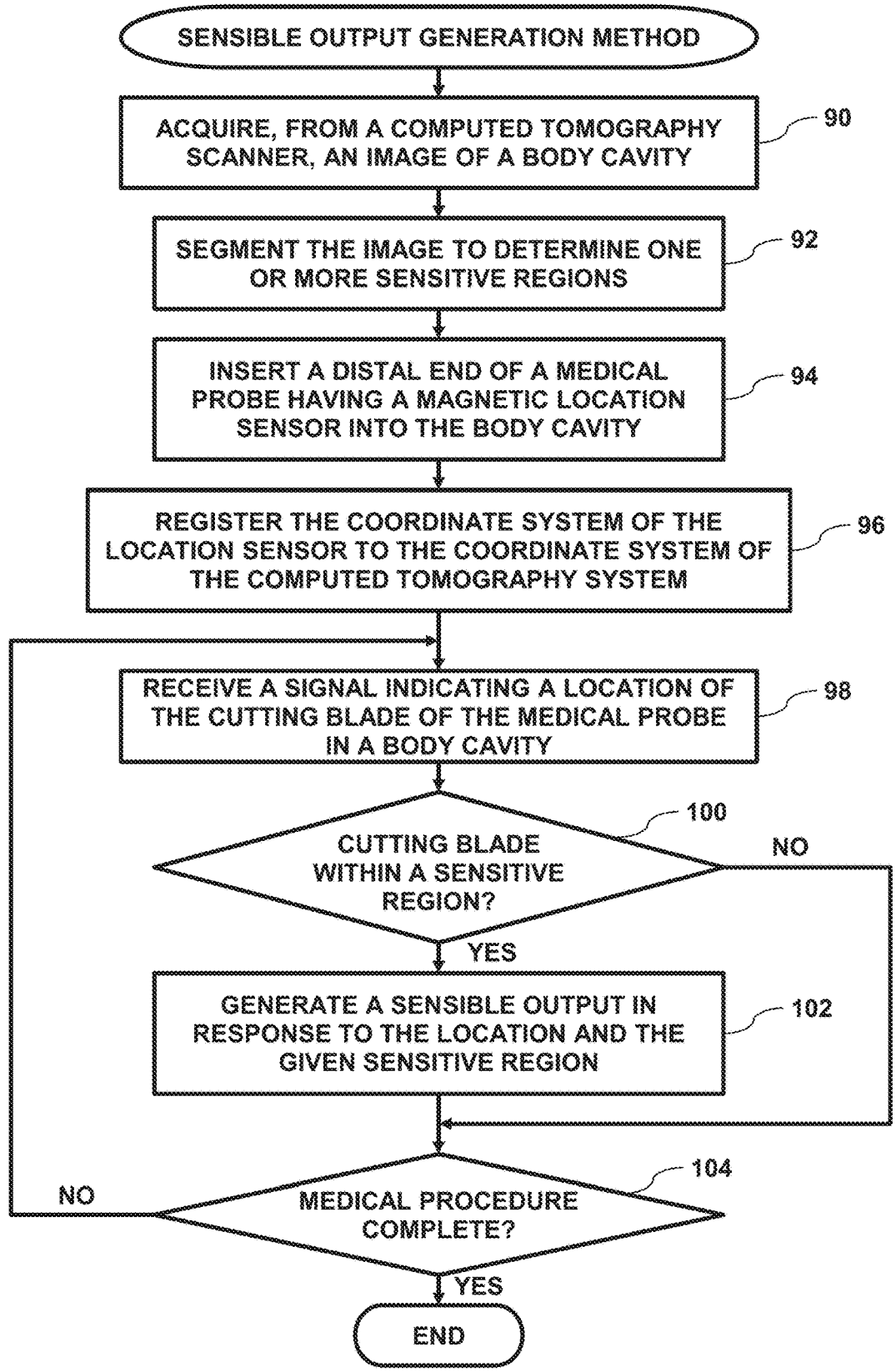
FIG. 2 is a flow diagram that schematically illustrates a method of generating, by the medical probe, a sensible output when a cutting blade on the medical probe is in proximity to a sensitive region in a patient, in accordance with an embodiment of the present invention.
Figure 4:
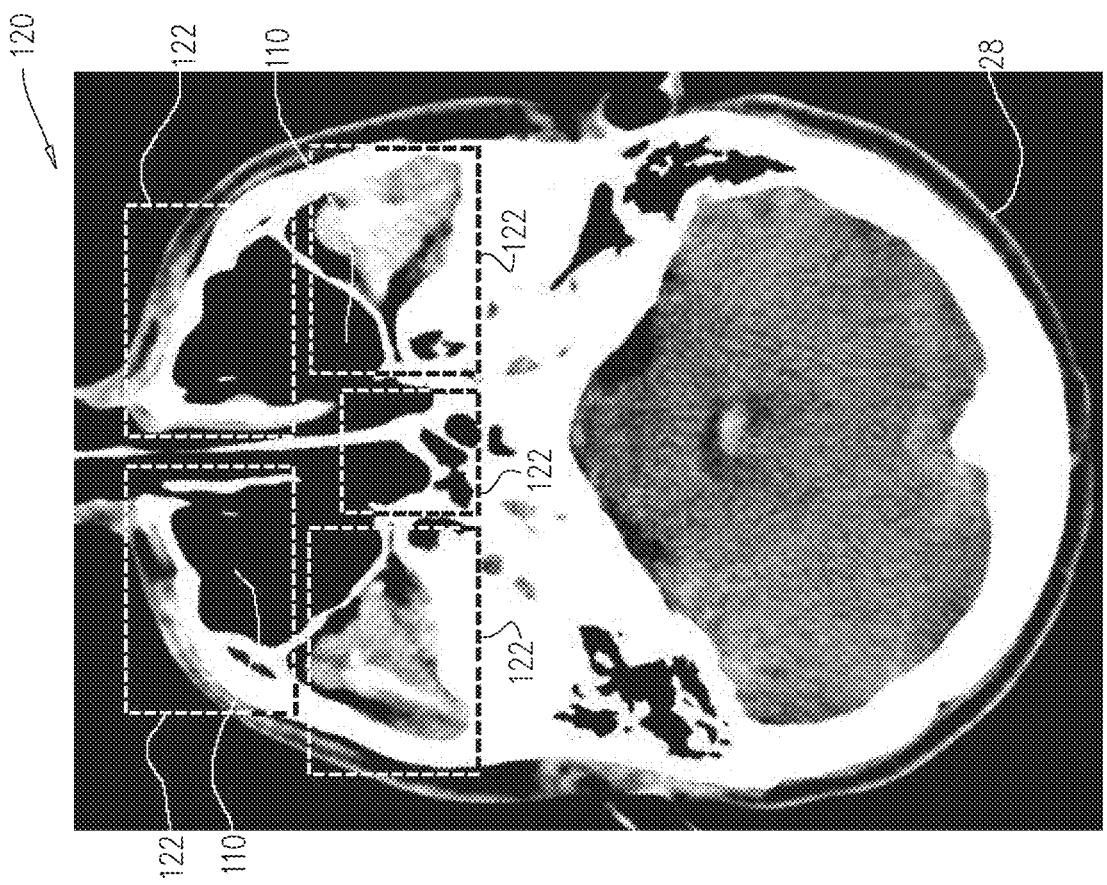
FIG. 4 is a schematic pictorial illustration showing an image slice of a three-dimensional computed tomography (CT) image of the patient generated in response to receiving image data from a CT scanner, in accordance with an embodiment of the present invention.
Figure 3:
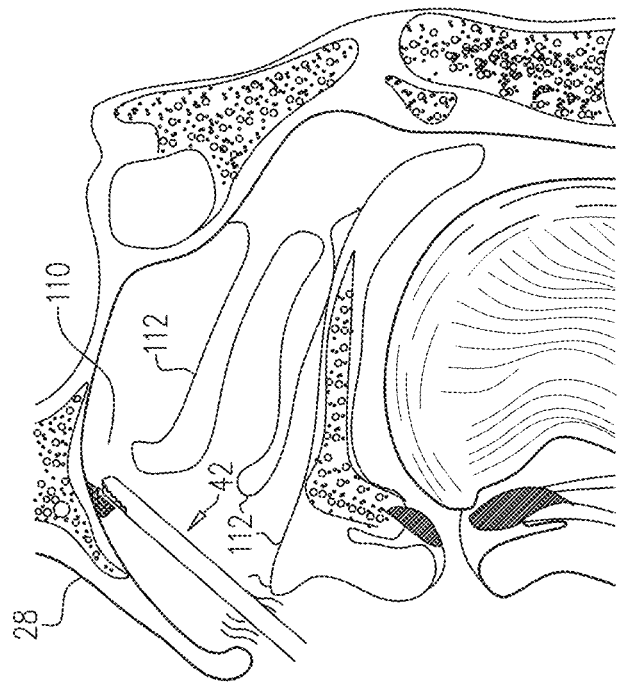
FIG. 3 is a schematic detail view showing a distal end of the medical probe inserted into a sinus cavity of the patient, in accordance with an embodiment of the present invention.

FIG. 2 is a flow diagram that schematically illustrates a method of generating, by medical probe 22, a sensible output when cutting blade 76 is in proximity to a sensitive region in patient 28, FIG. 3 is a schematic detail view showing distal end 42 inserted into a sinus cavity 110 of the patient, and FIG. 4 is a schematic pictorial illustration showing an image slice 120 of a three-dimensional computed tomography image that processor 44 generates in response to receiving image data from computed tomography scanner 23, in accordance with embodiments of the present invention. As shown in FIG. 3, patient 28 has multiple anatomical structures 112, and in embodiments of the present invention, the sensitive region comprises a given anatomical structure 112, such as an eye, a nerve (e.g., an optic nerve), or an artery (e.g., the carotid artery).

In an acquisition step 90, processor 44 acquires three-dimensional (3D) image data from computed tomography scanner 24, stores the image data to memory 50, and generates, based on the acquired image data, a three-dimensional image. While embodiments herein describe acquiring the 3D image data from computed tomography scanner 24, acquiring the 3D image data from any other type of medical imaging system is considered to be within the spirit and scope of the present invention.

In a segmentation step 92, processor 44 segments the received 3D image into multiple segments 122, and determines respective 3D locations of the segments. In operation, each segment 122 may comprise at least one anatomical structure 112. In an alternative embodiment, processor 44 can present image slice 120 as image 46 on display 48, and operator 40 can use input devices 52 to manually delineate the image slice (i.e., the 3D image) into segments 122. In some embodiments, a given sensitive region may comprise one or more segments 122.

The 3D image of patient 28 produced by CT scanner 24 typically comprises different gray scales to represent different tissue radiodensities (e.g., for bone tissue, nerve tissue and brain tissue) in the patient. To automatically segment the received 3D image into multiple segments 122, processor 44 can first detect a recognizable feature of a given anatomical structure 112 in patient 28, and then analyze radiodensities of tissue in proximity to the identified feature. For example, to segment an eye and an optic nerve in the received 3D image, processor 44 can:
  Identify an eye socket by its shape and a first radiodensity indicating bone.
  Identify the eye as a spherical shape in the eye socket having a second radiodensity indicating sclera tissue.
  Identify the optic nerve as tissue extending from the eye having a third radiodensity indicating nerve tissue.
  Segment a first segment comprising the eye socket and eye, and a second segment comprising the optic nerve.

Alternatively or additionally, operator 40 can manually segment the received 3D image by:
  Identifying a recognizable feature of a given anatomical structure 112 (e.g., the eye socket) in a given slice 120 of the 3D image presented in image 46.
  Identifying the optic nerve by identifying, in the given slice, tissue having a radiodensity indicating nerve tissue that extends from the eye socket.
  Manipulating input device(s) 52 to delineate and select (i.e., on image 46) a given segment 122 that includes the identified tissue (i.e., the optic nerve).

Steps 90 and 92 are typically performed prior to a medical procedure to be performed on patient 28. To initiate the medical procedure, operator 40 manipulates handle 38 so that, in an insertion step 94, distal end 42 enters a body cavity in patient 28.

In a registration step 96, processor 44 registers image coordinate system 30 to sensor coordinate system 60, and in a receiving step 98, the processor receives signals from magnetic field sensor 58 indicating a location of cutting blade 76 in the body cavity. In some embodiments, processor 44 can compute, based on the received signals, a location of position sensor 58, and add a vector (determined by a previously performed calibration) to the computed location to determine the location of cutting blade 76. In some embodiments, processor 44 can also determine an orientation of cutting blade 76.

To register the coordinate systems, processor 44 can present image 46 on display 48, and operator 40 can manipulate handle 38 so that distal tip 72 engages an identifiable feature of patient 28 (e.g., an ostium sinus coronary, also known as an orifice of coronary sinus or simply "OS") that is in the image and has an image location in image coordinate system 30. When distal tip 72 engages a given identifiable feature (e.g., a given anatomical structure) in image 46, operator 40 can select the given identifiable feature (e.g., by manipulating a given input device 52 to position, on the display, a cursor over the given identifiable feature). Upon receiving the registration signal, processor 44 can determine, based on signals received from position sensor 58, a magnetic location of the distal tip in sensor coordinate system 60. Processor 44 can compute, based on the magnetic and the image locations, a registration vector that can be used to register image coordinate system 30 to sensor coordinate system 60.

As described hereinbelow, processor 44 is configured to convey different activation signals to warning device 80, and the warning device is configured to generate different types of visual and or audio sensible outputs in response to the conveyed activation signal. In a first comparison step 100, if the location of cutting blade 76 is within a given sensitive region (i.e., the cutting blade is in proximity to a given anatomical structure 112 in the given sensitive region), then processor 44 can convey a given activation signal to warning device 80, and upon receiving the given activation signal, the warning device can generate a given sensible output in a generation step 102.

In embodiments of the present invention, the activation signals and the sensible outputs are responsive to the given sensitive region and the location of cutting blade 76 within the given sensitive region. In other words, processor 44 can convey different activation signals to warning device 80 based on (a) a given anatomical structure in proximity to cutting blade 76, and (b) a distance between the cutting blade and the given anatomical structure.

In one embodiment, the anatomical structures comprise blood vessels and nerves, and processor 44 can assign a high importance level to arteries (e.g., the carotid artery), a medium importance level to nerves (e.g., an optic nerve), and a low importance level to empty space in the body cavity, and convey different activation signals based on the respective importance levels. For example, if warning device 80 comprises a light emitting diode (LED), the LED can be configured to:

Emit red light upon receiving a first activation signal indicating that cutting blade 76 is in proximity to an artery.

Emit yellow light upon receiving a medium importance activation signal indicating that cutting blade 76 is in proximity to a nerve.

Emit green light upon receiving a low importance activation signal indicating that cutting blade 76 is not in proximity to any critical anatomical structures 112 (e.g., arteries or nerves).

In another example, warning device 80 comprises an audio generating device (i.e., circuitry and a speaker) that can generate audio output comprising synthesized speech that identifies a given anatomical structure 112 (e.g., "optic nerve") and a distance between blade 76 and the given anatomical structure (e.g., "five millimeters"). In a further example, warning device 80 may comprise a probe display (e.g., an LED screen) mounted on the handle, and processor 44 can present the given anatomical structure and the distance on the probe display (e.g., "Brain 5 mm").

In some embodiments, warning device 80 can be configured to convey additional sensible outputs indicating a distance to a given anatomical structure 112. Continuing the example where warning device 80 comprises an LED, the LED can blink faster if the received the activation signal indicates that the cutting blade is moving closer to the given anatomical structure, and blink slower if the received the activation signal indicates that the cutting blade is moving away from the given anatomical structure. As described supra, the different sensible outputs may also comprise different sounds.

Additionally or alternatively, processor 44 can present the given sensible output on display 48. To present the given sensible output on display 48 processor 44 can present, on the display, a message (e.g., an icon representing a given anatomical structure 112) with different visual effects (e.g., colors, intensity, size or blinking frequency) to indicate the current distance between the cutting blade and a given anatomical structure 112. The message on display 48 may also include text identifying a given anatomical structure 112 and a distance between the cutting blade and the given anatomical structure 112 (e.g., "Brain 5 mm").

In further embodiments, processor 44 can adjust a speed of motor 78 (and therefore the rotation speed of cutting blade 76) based on the distance between the cutting blade and a given anatomical structure 112. For example, processor 44 can reduce the speed of the motor as the cutting blade approaches a given anatomical structure (e.g., an artery or a nerve as described supra). In some embodiments, processor 44 can turn off motor 78 when cutting blade is very close (e.g., 2 mm) to an anatomical structure such as the carotid artery or an eye. In other words, processor 44 can control motor 78 so that the speed of the motor is directly related to the distance between cutting blade 76 and a given anatomical structure 112 (i.e., higher speeds at greater distances and lower speeds at smaller distances).

Finally, in a second comparison step 104, if the medical procedure is complete, then the method ends. If the medical procedure is not complete, then the method continues with step 98. Returning to step 100, if the location of cutting blade 76 is not within a given sensitive region, then the method continues with step 104.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
   (a) an insertion tube comprising a proximal end, and a distal end for insertion into a body cavity comprising one or more anatomical structures;
   (b) a cutting blade mounted at the distal end of the insertion tube;
   (c) a handle affixed to the proximal end and comprising a warning device which generates different sensible outputs in response to receiving different activation signals;
   (d) a position sensor fixed in a predefined disposition relative to the insertion tube; and
   (e) a processor configured to:
      (i) acquire, from an imaging system, a three-dimensional (3D) image of the body cavity,
      (ii) automatically identify, based on the 3D image and an anatomical structure dataset, respective 3D structure locations for each of the one or more anatomical structures, wherein the anatomical structure dataset describes one or more tissue shapes and one or more tissue radiodensities associated with a plurality of anatomical structures,
      (iii) when automatically identifying respective 3D structure locations for each of the one or more anatomical structures:
         (A) identify a first recognizable feature based on the anatomical structure dataset, and
         (B) identify a second recognizable feature proximate to the first recognizable feature based on its relative position and the anatomical structure dataset,
      (iv) receive, from the position sensor, a position signal indicative of a 3D blade location of the cutting blade within the body cavity,
      (v) determine, based on the 3D blade location and the respective 3D structure locations, a proximity of the cutting blade to a given anatomical structure, and
      (vi) convey, to the warning device, a given activation signal in response to the determined proximity to the given anatomical structure.

2. The medical apparatus according to claim 1, wherein the warning device is detachable from the handle.

3. The medical apparatus according to claim 1, wherein the warning device comprises an illumination device or an audio generating device.

4. The medical apparatus according to claim 3, wherein the sensible output generated by the illumination device in response to the determined proximity to the given anatomical structure comprises light having different colors, different intensities, or different durations.

5. The medical apparatus according to claim 3, wherein the sensible output generated by the audio generating device in response to the determined proximity to the given anatomical structure comprises sounds having different tones, different frequencies, different volumes, different durations, different rates of recurrence or different synthesized words.

6. The medical apparatus according claim 1, and comprising a display, and wherein the processor is configured to present, on the display:
   (i) the sensible output in response to the determined proximity to the given anatomical structure, and
   (ii) a numerical distance that describes the proximity of the cutting blade to the given anatomical structure.

7. The medical apparatus according to claim 1, wherein the position sensor comprises a triaxial coil, and wherein the processor is configured to:
 (i) after the distal end engages an anatomical structure for which there is a 3D structure location, receive a selection from a user of the 3D structure location engaged by the distal end; and
 (ii) register the sensor coordinate system to the image coordinate system based on a registration vector determined from the 3D structure location and the signal indicative of the 3D blade location at the time the selection from the user is received.

8. The medical apparatus according to claim 1, wherein the imaging system comprises a computed tomography scanner.

9. The medical apparatus according to claim 1, wherein the imaging system comprises an image coordinate system, wherein the position sensor comprises a sensor coordinate system, and wherein prior to receiving the position signal indicative of a 3D blade location of the cutting blade within the body cavity, the processor is configured to register the sensor coordinate system to the image coordinate system.

10. The medical apparatus according to claim 1, and comprising a motor mounted within the handle and configured to rotate the cutting blade at a plurality of rotation speeds, and wherein the processor is configured to reduce the rotation speed of the cutting blade as the cutting blade approaches a given anatomical structure.

11. The medical apparatus according to claim 1, wherein the processor is configured to formulate an identification of a given segment of the multiple segments, and wherein the activation signal comprises the identification.

12. The medical apparatus of claim 1, wherein the processor is further configured to:
 (i) analyze a set of tissue radiodensities proximate to the first recognizable feature within the 3D image when identifying the second recognizable feature,
 (ii) identify the first recognizable feature based on a first tissue shape within the 3D image, a first tissue radiodensity within the 3D image, and the anatomical structure dataset,
 (iii) identify the second recognizable feature based on a second tissue shape within the 3D image, a second tissue radiodensity within the 3D image, the relative position of the second recognizable feature to the first recognizable feature, and the anatomical structure dataset, and
 (iv) use the location of the second recognizable feature as that respective 3D structure location.

13. A method, comprising:
 (a) acquiring, from an imaging system, a three-dimensional (3D) image of a body cavity comprising one or more anatomical structures;
 (b) automatically identifying, based on the 3D image and an anatomical structure dataset, respective 3D structure locations for each of the one or more anatomical structures, wherein the anatomical structure dataset describes one or more tissue shapes and one or more tissue radiodensities associated with a plurality of anatomical structures;
 (c) when automatically identifying respective 3D structure locations for each of the one or more anatomical structures:
  (i) identifying a first recognizable feature based on the anatomical structure dataset, and
  (ii) identifying a second recognizable feature proximate to the first recognizable feature based on its relative position and the anatomical structure dataset,
 (c) receiving, from a medical probe having an insertion tube and a position sensor fixed in a predefined disposition relative to the insertion tube, a position signal indicative of a 3D location of a cutting blade mounted at a distal end of the insertion tube and inserted into the body cavity;
 (e) determining, by a processor based on the 3D blade location and the respective 3D structure locations, a proximity of the cutting blade to a given anatomical structure;
 (f) conveying, to a warning device mounted on a handle affixed to a proximal end of the insertion tube and configured to generate different sensible outputs in response to receiving different activation signals, a given activation signal in response to the determined proximity to the given anatomical structure;
 (g) receiving, by the warning device, the given activation signal; and
 (h) generating, by the warning device, a given sensible output in response to the received activation signal.

14. The method according to claim 13, wherein the warning device is detachable from the handle.

15. The method according to claim 13, wherein the warning device comprises an illumination device or an audio generating device.

16. The method according to claim 15, wherein the sensible output generated by the illumination device in response to the determined proximity to the given anatomical structure comprises light having different colors, different intensities, or different durations.

17. The method according to claim 15, wherein the sensible output generated by the audio generating device in response to the determined proximity to the given anatomical structure comprises sounds having different tones, different frequencies, different volumes, different durations, different rates of recurrence or different synthesized words.

18. The method according claim 13, and comprising presenting, on a display:
 (i) the sensible output in response to the determined proximity to the given anatomical structure, and
 (ii) a numerical distance that describes the proximity of the cutting blade to the given anatomical structure.

19. The method according to claim 13, wherein the position sensor comprises a triaxial coil, the method further comprising:
 (i) after the distal end engages an anatomical structure for which there is a 3D structure location, receiving a selection from a user of the 3D structure location engaged by the distal end; and
 (ii) registering the sensor coordinate system to the image coordinate system based on a registration vector determined from the 3D structure location and the signal indicative of the 3D blade location at the time the selection from the user is received.

20. The method according to claim 13, wherein the imaging system comprises a computed tomography scanner.

21. The method according to claim 13, wherein the imaging system comprises an image coordinate system, wherein the position sensor comprises a sensor coordinate system, and comprising registering, prior to receiving the position signal indicative of a 3D blade location of the cutting blade within the body cavity, the sensor coordinate system to the image coordinate system.

22. The method according to claim 13, wherein the medical probe comprises a motor mounted within the handle and configured to rotate the cutting blade at a plurality of rotation speeds, and comprising reducing the rotation speed of the cutting blade as the cutting blade approaches a given anatomical structure.

23. The method according to claim 13, and comprising formulating an identification of a given segment of the multiple segments, and wherein the activation signal comprises the identification.

24. The method of claim 13, further comprising:
(a) analyzing a set of tissue radiodensities proximate to the first recognizable feature within the 3D image when identifying the second recognizable feature,
(b) identifying the first recognizable feature based on a first tissue shape within the 3D image, a first tissue radiodensity within the 3D image, and the anatomical structure dataset,
(c) identifying the second recognizable feature based on a second tissue shape within the 3D image, a second tissue radiodensity within the 3D image, the relative position of the second recognizable feature to the first recognizable feature, and the anatomical structure dataset, and
(d) using the location of the second recognizable feature as that respective 3D structure location.

25. A computer software product, operated in conjunction with a medical probe having an insertion tube and a position sensor fixed in a predefined disposition relative to the insertion tube, the product comprising a non-transitory computer-readable medium, in which program instructions are stored, which instructions, when read by a computer, cause the computer to:
(a) acquire, from an imaging system, a three-dimensional (3D) image of a body cavity comprising one or more anatomical structures;
(b) automatically identify, based on the 3D image and an anatomical structure dataset, respective 3D structure locations for each of the one or more anatomical structures, wherein the anatomical structure dataset describes one or more tissue shapes and one or more tissue radiodensities associated with a plurality of anatomical structures;
(c) when automatically identifying respective 3D structure locations for each of the one or more anatomical structures:
(i) identify a first recognizable feature of an anatomical structure based on a first tissue shape within the 3D image, a first tissue radiodensity within the 3D image, and the anatomical structure dataset,
(ii) analyze a set of tissue radiodensities proximate to the first recognizable feature within the 3D image,
(iii) identify a second recognizable feature proximate to the first recognizable feature based on a second tissue shape within the 3D image, a second tissue radiodensity within the 3D image, the position of the second recognizable feature relative to the first recognizable feature, and the anatomical structure dataset, and
(iv) use the location of the second recognizable feature as that respective 3D structure location,
(d) receive, from the position sensor, a position signal indicative of a 3D location of a cutting blade mounted at a distal end of the insertion tube and inserted into the body cavity;
(e) determine, based on the 3D blade location and the respective 3D structure locations, a proximity of the cutting blade to a given anatomical structure; and
(f) convey, to a warning device mounted on a handle affixed to a proximal end of the insertion tube and configured to generate a plurality of sensible outputs in response to receiving a corresponding plurality of activation signals, a given activation signal in response to the determined proximity to the given anatomical structure.

* * * * *

UNITED STATES PATENT AND TRADEMARK OFFICE
CERTIFICATE OF CORRECTION

PATENT NO.         : 10,813,657 B2
APPLICATION NO.    : 15/730578
DATED              : October 27, 2020
INVENTOR(S)        : Govari et al.

Page 1 of 1

It is certified that error appears in the above-identified patent and that said Letters Patent is hereby corrected as shown below:

In the Claims

Claim 13, Column 12, Line 4, reads "(c) receiving, from a …"; which should be deleted and replaced with "(d) receiving, from a …".

Signed and Sealed this
Twelfth Day of January, 2021

Andrei Iancu
*Director of the United States Patent and Trademark Office*